(12) United States Patent
O'Hare

(10) Patent No.: US 11,890,169 B1
(45) Date of Patent: Feb. 6, 2024

(54) DISTRIBUTED AIRFLOW APPARATUS

(71) Applicant: Curtis O'Hare, Cabot, AR (US)

(72) Inventor: Curtis O'Hare, Cabot, AR (US)

( * ) Notice: Subject to any disclaimer, the term of this patent is extended or adjusted under 35 U.S.C. 154(b) by 0 days.

(21) Appl. No.: 17/749,374

(22) Filed: May 20, 2022

Related U.S. Application Data

(60) Provisional application No. 63/191,684, filed on May 21, 2021.

(51) Int. Cl.
*A61F 13/00* (2006.01)

(52) U.S. Cl.
CPC ............... *A61F 13/00068* (2013.01)

(58) Field of Classification Search
CPC .......... A61F 13/00068; A61F 13/00051; A61F 13/0206; A61F 13/046; A61M 13/00; A61M 13/003; A61M 13/006; A61M 2027/004; A61M 25/00; A61M 27/00; A61M 27/002; A61M 35/00; A61M 35/30; A61M 39/00
See application file for complete search history.

(56) References Cited

U.S. PATENT DOCUMENTS

| | | | | |
|---|---|---|---|---|
| 4,387,710 A | * | 6/1983 | Beatty, III | A61F 13/046 602/14 |
| 2004/0162511 A1 | * | 8/2004 | Barberio | A61F 5/01 602/14 |
| 2010/0268136 A1 | * | 10/2010 | Der Ovanesian | A61F 5/0104 602/14 |
| 2017/0246039 A1 | * | 8/2017 | Wu | A61M 1/918 |
| 2019/0314595 A1 | * | 10/2019 | Dube | A61M 16/20 |
| 2020/0368074 A1 | * | 11/2020 | Cole | A61F 13/00063 |

\* cited by examiner

*Primary Examiner* — Leslie A Lopez
*Assistant Examiner* — Jihad Dakkak

(57) ABSTRACT

A device for delivering air or other gas into the area of a skin fold in order to dry the skin and thereby prevent the development of inflammation, rash, or infection features an air manifold that connects to an air or pressurized gas source. The manifold delivers air to a distribution layer, which then distributes air along the length of the skin fold when the layer is within the fold. The distribution layer is formed of a gauze material, with a plurality of tubular longitudinal sections of gauze connected by flat sections of gauze. The distribution layer is fitted between a top and bottom half of the manifold, held fast by spikes extending from within the halves.

16 Claims, 3 Drawing Sheets

DISTRIBUTED AIRFLOW APPARATUS

CROSS-REFERENCE TO RELATED APPLICATIONS

This application claims the benefit of U.S. provisional patent application no. 63/191,684, filed on May 21, 2021. Such application is incorporated herein by reference in its entirety.

BACKGROUND

Intertrigo is a common form of skin irritation that may lead to rashes. It occurs in warm, moist areas of the human skin where airflow is limited. It usually develops between folds of skin, such as where two skin surfaces are rubbing together. Bacteria, fungi, and yeasts thrive in the warm, moist environment between skin folds, which often leads to secondary infections.

Common treatments for intertrigo include steroidal creams, oral or topical antibiotics, and antifungal medications. In addition, there are moisture-wicking fabrics that have been developed for placement into the area of the skin fold. Some of these fabrics include antimicrobials, such as antimicrobial silver. But the problem could be avoided entirely if proper airflow is maintained in the area of the skin folds. Air flow would keep the area between the folds clean and dry, thereby making the area inhospitable to the sorts of bacteria, fungi, and yeasts that cause this condition. It may be seen then that an apparatus capable of providing proper airflow within the area of skin folds, while also maintaining patient comfort, would be highly advantageous.

References mentioned in this background section are not admitted to be prior art with respect to the present invention.

SUMMARY

The present invention is directed to an apparatus for continuously or intermittently delivering air or other gas into the area of a skin fold in order to maintain dryness of the skin and prevent the development of inflammation, rash, or infection. Because gas is continuously or intermittently introduced to the skin fold of the patient in a distributed fashion, dryness is maintained for long periods and thus conditions such as intertrigo may be prevented. The present invention, in certain embodiments, may include an air manifold that connects to an air or pressurized gas source. The manifold delivers air to a distribution layer, which then distributes air along the length of the skin fold. The distribution layer may be formed of a gauze material, with a plurality of tubular longitudinal sections of gauze connected by flat sections of gauze. The tubular longitudinal sections of gauze hold the skin fold slightly apart such that air flow is not disrupted in the area, while also maintaining patient comfort. The gauze material allows for an even distribution of air throughout the area of the skin fold in order to maintain uniform dryness.

These and other features, objects and advantages of the present invention will become better understood from a consideration of the following detailed description of the preferred embodiments and appended claims in conjunction with the drawings as described following:

DRAWINGS

DETAILED DESCRIPTION

Before the present invention is described in further detail, it should be understood that the invention is not limited to the particular embodiments described or the particular applications described, and that the terms used in describing the particular embodiments are for the purpose of describing those particular embodiments only, and are not intended to be limiting, since the scope of the present invention will be limited only by the claims.

The purpose of the invention is to provide a continuous or intermittent flow of air or other gas in the area of a skin fold. The various embodiments of the invention may be particularly useful in a hospital setting, where a continuous flow of gas is generally provided at bedside for various medical purposes. The invention is not so limited, however, and could be used where a portable supply of continuous or intermittent air or other gas is used, such as from a compressed gas tank or an air compressor. The invention thus could be used in almost any environment, even environments where electrical power is not available, since the invention may be powered by compressed gas tanks. In addition, the invention may be used in applications other than in the prevention of irritation or infection within skin folds. The invention could, in fact, be applied in any circumstance or environment where a continuous or intermittent flow of distributed air or other gas is advantageous or desired.

Figure 1:
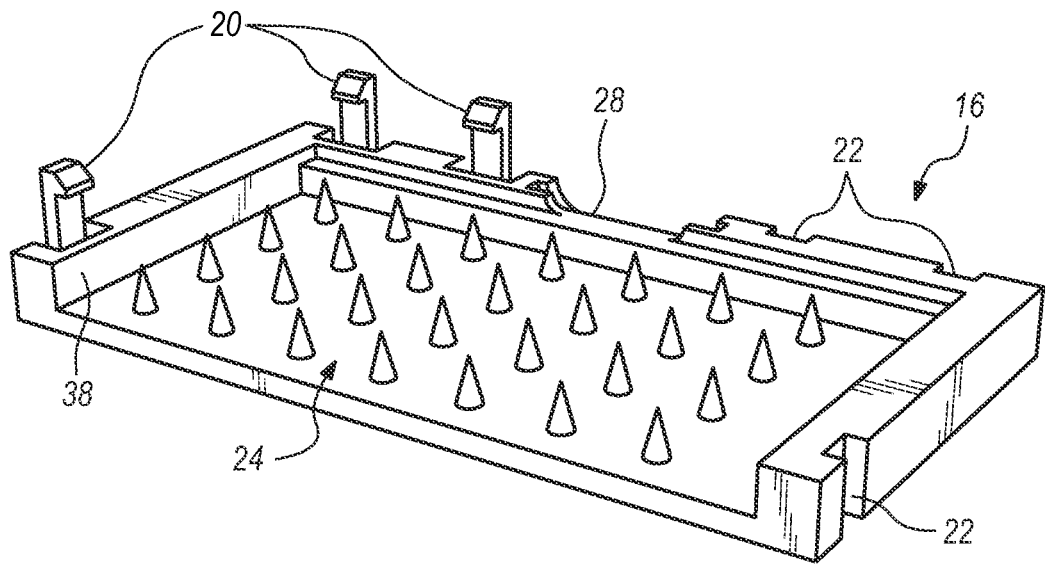
FIG. 1 is a perspective view of a bottom half of a manifold according to an embodiment of the invention.
Figure 2:
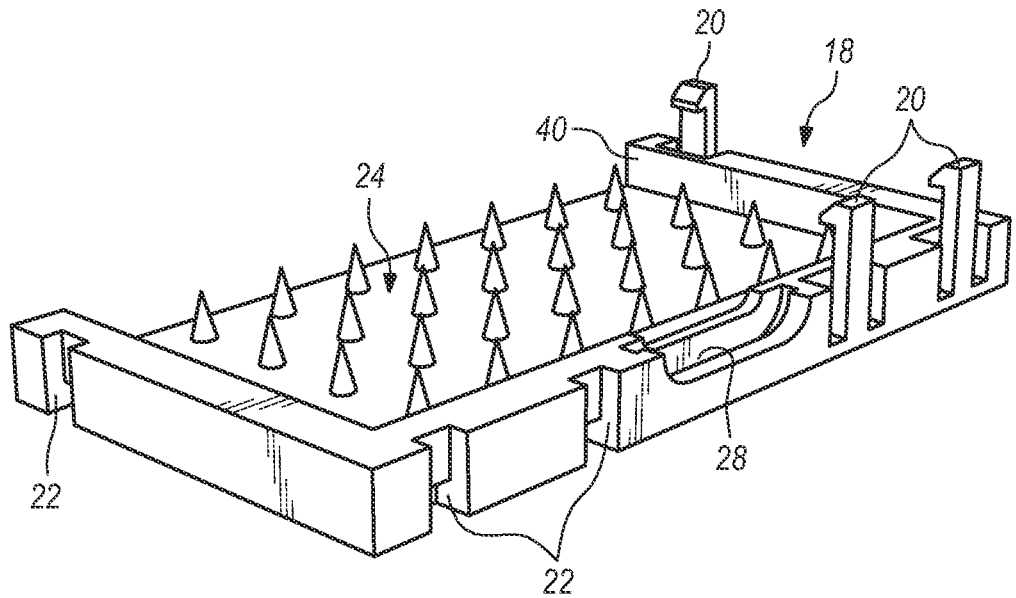
FIG. 2 is a perspective view of a top half of a manifold according to an embodiment of the invention.
Figure 6:
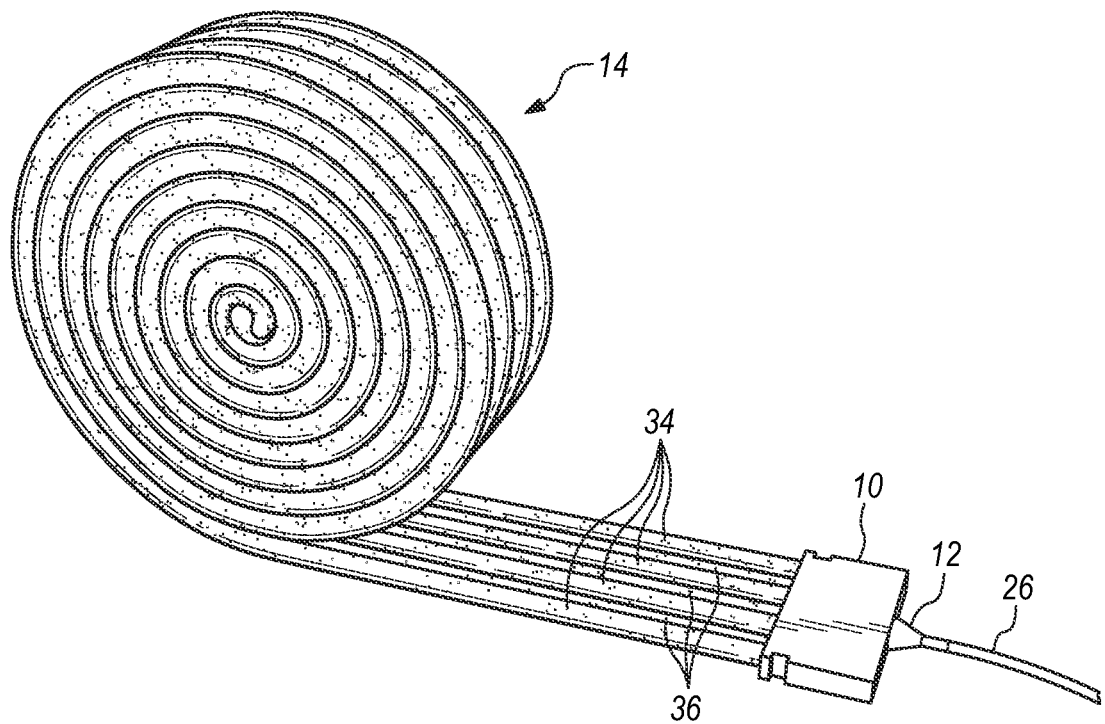
FIG. 6 is a perspective view of an assembled manifold with gauze distribution layer according to an embodiment of the invention.

In overview, the invention consists of a manifold 10, a manifold air connector 12, and a gauze distribution layer 14, as shown in FIG. 6. FIGS. 1 and 2 show the top half 16 and bottom half 18, respectively, of an embodiment of the manifold 10. It may be seen that the manifold halves 16 and 18 include snap-lock tabs 20 and opposing slots 22 in order to hold the manifold 10 together when assembled. Manifold 10 includes a series of spikes 24 within the interior of the manifold; the purpose of spikes 24 is to capture and hold an end of the gauze distribution layer 14 in place when the device is assembled. Spikes 24 may extend from both top 16 and bottom 18, or from either one alone, in various embodiments. Manifold 10 serves to distribute air flow along the width of gauze distribution layer 14. Manifold 10 has a smaller inlet but a larger outlet of a matching width with gauze distribution layer 14.

Manifold top 16 features top wall 38 passing along three sides of its inner surface. Likewise, manifold bottom 18 features bottom wall 40 passing along three sides of its inner surface. Spikes 24 are arranged within the perimeter of top wall 38 and bottom wall 40. In addition, tabs 20 and slots 22 are positioned at top wall 38 and bottom wall 40.

In order to assemble the device for use, one half of manifold 10 is presented (either top 16 or bottom 18), an end of gauze distribution layer 14 is then placed flat onto the surface of top 16 or bottom 18 such that spikes 24 pass through the gauze distribution layer 14, and then top 16 and bottom 18 are snapped together over the end of the gauze distribution layer 14. It may be seen then that top wall 38 engages with bottom wall 40, providing a space within top 16 and bottom 18 that receives the end of gauze distribution layer 14. The open side of manifold formed thereby allows for the passage of gauze distribution layer 14 out of manifold 10. Spikes 24 hold gauze distribution layer 14 in place with respect to manifold 10.

Top 16 and 18 are held together by the engagement of tabs 20 and slots 22. Gauze distribution layer 14 will then be held fast for so long as manifold 10 remains assembled, but gauze distribution layer 14 can be easily removed and replaced by simply pulling manifold 10 apart (separating top 16 and bottom 18 by disengaging tabs 20 from slots 22) and removing the captured end of gauze distribution layer 14 from top 16 and bottom 18. In this way, soiled gauze distribution layer 14 may be replaced by a fresh length of gauze distribution layer 14.

Figure 3:
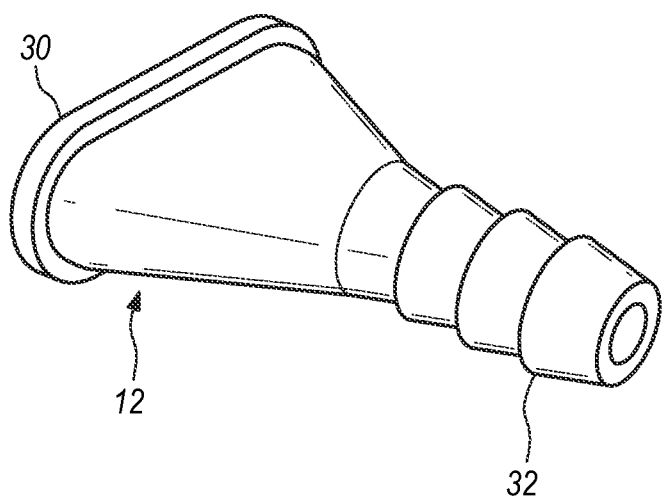
FIG. 3 is a perspective view of a manifold air connector according to an embodiment of the invention.

Manifold air connector 12, shown in detail in FIG. 3, provides a connection point for tubing 26, which provides air or other gas into manifold 10 and then through gauze distribution layer 14. Each of manifold top 16 and manifold bottom 18 include a recess 28 to receive a lip 30 extending around the proximal flared end of manifold air connector 12. Manifold air connector 12 may be slipped into place before top 16 and bottom 18 of manifold 10 are snapped together, and will thereby be held fast when the device is assembled. Alternatively, manifold air connector 12 could be integrally formed with either of manifold top 16 or manifold bottom 18, or permanently connected to one of manifold top 16 or manifold bottom 18 such as by glue or fasteners.

Figure 4:
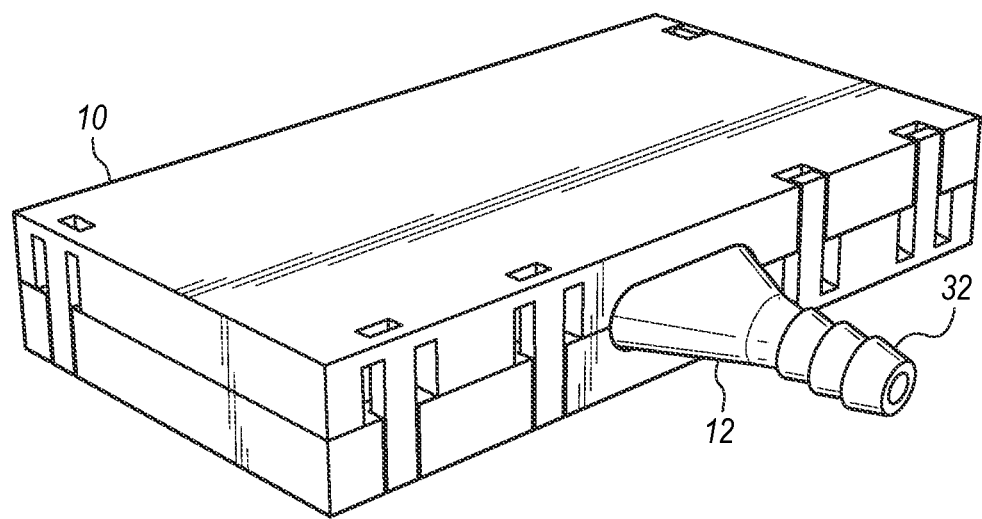
FIG. 4 is a perspective rear view of an assembled manifold according to an embodiment of the invention.
Figure 5:
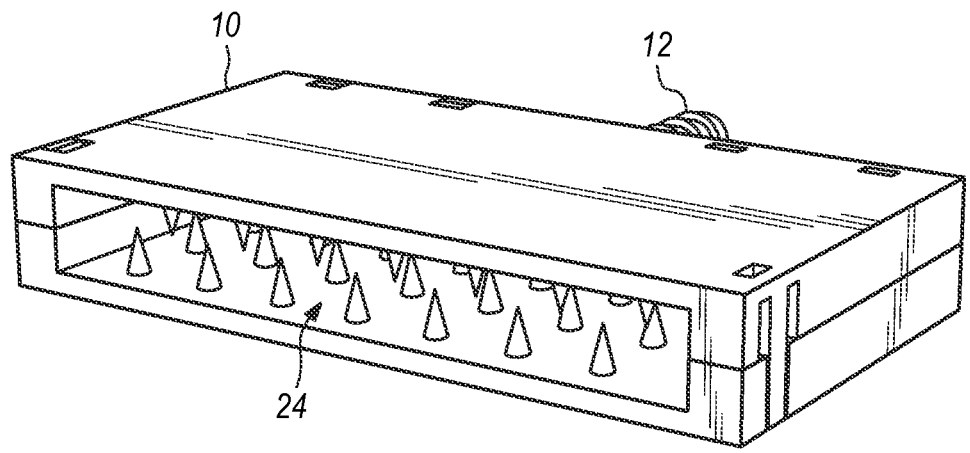
FIG. 5 is a perspective front view of an assembled manifold according to an embodiment of the invention.

The distal end of manifold air connector 12, which connects to tubing 26, features a series of barbs 32. The purpose of barbs 32 is to allow tubing 26 to easily engage with manifold air connector 12 yet hold tubing 26 firmly in place once the connection is made. Barbs 32 may be of various sizes to accommodate various sizes of tubing 26. The assembled manifold 10 and air manifold connector 12 are depicted in FIGS. 4 and 5 (shown without gauze distribution layer 14 for clarity in these figures).

FIG. 6 shows the fully assembled apparatus, including gauze distribution layer 14. Gauze distribution layer 14 may be formed of light, open-weave cotton. Other materials may be used such as silk, synthetical materials such as rayon or polyester, or any other appropriate material that allows the passage of air or gas as described herein. As may be seen, gauze distribution layer 14 is formed of a plurality of gauze tubes 34 through which air or other gas may pass longitudinally while being distributed along gauze distribution layer 14. Four gauze tubes 34 are illustrated, but any number or size of gauze tubes 34 may be employed in varying sizes and widths of gauze distribution layer 14, as best adapted to a particular application. Gauze tubes 34 provide a spacing effect, such that the opposing sides of the skin fold are held apart when gauze distribution layer 14 is positioned within the skin fold. Gauze tubes 34 are sufficiently rigid to provide at least some spacing in the skin fold. This spacing furthers the dissipation of moisture within the skin fold, thereby preventing infection and other issues. In addition, gauze tubes 34 facilitate the distribution of air or gas along distribution layer 14 by allowing air or gas to pass therethrough, and thus serve to more evenly distribute air or gas within the skin fold along the entire length of gauze distribution layer 14.

Gauze tubes 34 are connected by flat gauze sections 36. Although three flat gauze sections 36 are shown connecting four gauze tubes 34 in FIG. 6, any size and number of flat gauze sections 36 may be used to connect gauze tubes 34 in various alternative embodiments. Air or gas may pass between gauze tubes 34 by passing through flat gauze sections 36, thereby serving to equalize distribution of air or gas laterally along gauze distribution layer 14, and thus all along the area of the skin fold. In addition, flat gauze sections 36 may serve to absorb moisture that accumulates within the skin fold. This moisture may then be evaporated more easily by the air or gas passing through flat gauze sections 36 after such moisture is absorbed, thereby removing the moisture from the skin and thus preventing infection or other issues.

In certain embodiments, gauze distribution layer 14 is provided as a roll for ease of use. The provider or user may simply insert one end of gauze distribution layer 14 into manifold 10 as described above, then unroll gauze distribution layer 14 to the desired length for a particular application. The provider or user may then cut gauze distribution layer 14 at this desired length and proceed to use the apparatus. Alternatively, gauze distribution layer 14 may be cut to length before assembly. In either event, if the gauze becomes soiled during use then manifold 10 may be disassembled, the new end of the gauze layer roll inserted into manifold 10 and reassembled, again cut to length, and the use of the device may easily proceed. As an alternative to a roll, gauze distribution layer 14 could be provided in pre-cut sections of any desired length, as preset based on particular target applications.

Unless otherwise stated, all technical and scientific terms used herein have the same meaning as commonly understood by one of ordinary skill in the art to which this invention belongs. Although any methods and materials similar or equivalent to those described herein can also be used in the practice or testing of the present invention, a limited number of the exemplary methods and materials are described herein. It will be apparent to those skilled in the art that many more modifications are possible without departing from the inventive concepts herein.

All terms used herein should be interpreted in the broadest possible manner consistent with the context. When a grouping is used herein, all individual members of the group and all combinations and subcombinations possible of the group are intended to be individually included. When a range is stated herein, the range is intended to include all subranges and individual points within the range. All references cited herein are hereby incorporated by reference to the extent that there is no inconsistency with the disclosure of this specification.

The present invention has been described with reference to certain preferred and alternative embodiments that are intended to be exemplary only and not limiting to the full scope of the present invention, as set forth in the appended claims.

The invention claimed is:

1. A distributed airflow apparatus, comprising:
   a manifold adapted to distribute a gas flow, wherein the manifold comprises an inlet and an outlet, wherein the inlet is smaller in area than the outlet, wherein the manifold comprises a manifold top and a manifold bottom, and wherein at least one of the manifold top and the manifold bottom comprises a plurality of spikes extending within the manifold;
   a gauze distribution layer comprising a gauze distribution layer end, wherein the gauze distribution layer end is positioned between the manifold top and manifold bottom and wherein the plurality of spikes extending within the manifold extend through the gauze distribution layer end to hold the gauze distribution layer end within the manifold to receive the gas flow from the manifold, wherein the gauze distribute layer comprises a plurality of gauze tubes connected by at least one flat gauze section, whereby the gas flow is distributed longitudinally along the gauze distribution layer through the plurality of gauze tubes and laterally through the at least one flat gauze section.

2. The distributed airflow apparatus of claim 1, wherein both the manifold top and the manifold bottom comprise the plurality of spikes extending within the manifold.

3. The distributed airflow apparatus of claim 1, further comprising an air connector attached to the manifold to provide air flow into the manifold inlet.

4. The distributed airflow apparatus of claim 3, wherein the air connector comprises at least one barb at a distal end of the air connector to attach the air connector securely to a tubing.

5. The distributed airflow apparatus of claim 4, wherein the air connector comprises a lip at a proximal end of the air connector, and wherein the manifold comprises a recess sized to receive the air connector lip.

6. The distributed airflow apparatus of claim 1, wherein at least one of the manifold top and the manifold bottom comprises at least one tab.

7. The distributed airflow apparatus of claim 6, wherein at least one of the manifold top and the manifold bottom comprises at least one slot adapted to receive the at least one tab.

8. The distributed airflow apparatus of claim 7, wherein the manifold top comprises a manifold top wall at a perimeter of the manifold top.

9. The distributed airflow apparatus of claim 8, wherein the manifold bottom comprises a manifold bottom wall at a perimeter of the manifold bottom, wherein the manifold bottom is sized to fit to the manifold top.

10. The distributed airflow apparatus of claim 9, wherein the at least one tab is fitted at one of the manifold top and the manifold bottom, and the at least one slot is fitted at one of the manifold top and the manifold bottom.

11. The distributed airflow apparatus of claim 1, wherein the manifold outlet comprises a width, the gauze distribution layer comprises a width, and the manifold outlet width and gauze distribution layer width are equal.

12. The distributed airflow apparatus of claim 1, wherein the gauze distribution layer is formed of an open-weave cotton.

13. A gauze distribution layer for use with a distributed airflow apparatus, the gauze distribution layer comprising:
   a plurality of gauze tubes;
   at least one flat gauze section connecting the plurality of gauze tubes, whereby a gas flow through the gauze distribution layer may be distributed longitudinally along the gauze distribution layer through the plurality of gauze tubes and laterally through the at least one flat gauze section; and
   a flat gauze section end adapted to be fitted within a manifold comprising a manifold top, a manifold bottom, and a plurality of spikes extending within the manifold top and manifold bottom, wherein the flat gauze section end is pierced by the plurality of spikes to hold the flat gauze section end in place within the manifold, whereby the gas flow may be distributed from the manifold into the gauze distribution layer.

14. The gauze distribution layer of claim 13, wherein the gauze distribution layer is configured to be cut to a gauze distribution layer length equal to a length of a skin fold that the gauze distribution layer is configured to be positioned adjacent to.

15. The gauze distribution layer of claim 13, wherein the gauze distribution layer comprises an absorbent material.

16. The gauze distribution layer of claim 13, wherein the gauze distribution layer comprises open-weave cotton.

\* \* \* \* \*